United States Patent [19]
Singh et al.

[11] Patent Number: 5,744,009
[45] Date of Patent: Apr. 28, 1998

[54] METHOD AND APPARATUS FOR RECOVERING CONDENSABLES IN VAPOR FROM A UREA VACUUM EVAPORATOR

[75] Inventors: Vishnu Deo Singh, Sugarland; Richard Bruce Strait, Kingwood; Thomas Anthony Czuppon, Houston, all of Tex.

[73] Assignee: The M. W. Kellogg Company, Houston, Tex.

[21] Appl. No.: 499,510

[22] Filed: Jul. 7, 1995

[51] Int. Cl.$^6$ .............................. B01D 1/28; B01D 3/10
[52] U.S. Cl. .............................. 203/42; 203/73; 203/80; 203/DIG. 14; 95/232; 159/24.3; 159/47.2; 159/DIG. 16; 202/173; 202/183; 202/185.2; 202/205; 564/73
[58] Field of Search .............................. 203/42, 73, 80, 203/91, DIG. 9, DIG. 14; 159/24.3, 28.6, DIG. 16, 17.1, 47.2; 202/172, 182, 173, 205, 183, 185.2; 564/67, 73; 95/232

[56] References Cited

U.S. PATENT DOCUMENTS

| | | | |
|---|---|---|---|
| 2,682,499 | 6/1954 | Thurman | 202/183 |
| 3,711,544 | 1/1973 | Summerville | 203/42 |
| 3,985,523 | 10/1976 | Kaupas et al. | 55/70 |
| 4,003,801 | 1/1977 | Chikaoka et al. | 203/42 |
| 4,256,662 | 3/1981 | Gorlousky et al. | 564/67 |
| 4,311,856 | 1/1982 | Inoue et al. | 95/232 |

Primary Examiner—Virginia Manoharan
Attorney, Agent, or Firm—The M. W. Kellogg Company

[57] ABSTRACT

An improved urea recovery process is presented. In the improved process, multiple vacuum rated surface condensers used to condense water vapor evolved during urea vacuum evaporation/concentration are replaced by a direct contact cooler/absorber to obtain substantial capital and utility cost savings. Improved heat exchange efficiency of the present process significantly reduces cooling water usage in comparison to the surface condensers.

20 Claims, 4 Drawing Sheets

METHOD AND APPARATUS FOR RECOVERING CONDENSABLES IN VAPOR FROM A UREA VACUUM EVAPORATOR

FIELD OF THE INVENTION

The present invention relates to a urea recovery process, and more particularly a urea recovery process wherein condensables in a vapor stream removed overhead from a urea vacuum evaporator/concentrator are condensed using a contact cooler.

BACKGROUND OF THE INVENTION

Urea is typically made by directly combining ammonia and carbon dioxide to form ammonium carbamate. Ammonium carbamate is then dehydrated to form urea as an aqueous solution. The aqueous urea-containing stream is processed to separate unreacted components and concentrate the urea product in a series of depressurization and vacuum evaporation stages. Vapor evolved from the vacuum evaporation stages comprising primarily water, ammonia, carbon dioxide and urea carry-over is then cooled to produce an aqueous condensate which can be recycled for a variety of plant purposes. Concurrently, non-condensable gases comprising primarily nitrogen and oxygen are treated to remove residual ammonia prior to venting.

The evolved vapor is typically cooled by indirect surface exchangers generally designed for operation at a subatmospheric pressure. Several cooling stages are generally used. The aqueous condensate produced by each stage is typically directed to a central storage tank. Since the cooling stages can be operated at a higher pressure than an upstream evaporation stage or a downstream ammonia treatment stage, ejectors can be required to boost the pressure of the inlet and outlet gas streams.

Shell and tube coolers used to condense the vapor streams can often become fouled because urea carried over in the vapor streams and solid carbamate can build up on the surfaces of the tubes. If the coolers are not operating efficiently, vacuum evaporators having a higher than design pressure can result in a urea product having excessive water concentration. This can be detrimental for the urea handling area of the plant and especially in the case of a prilled urea product specification.

Applicants are unaware of contact coolers having been previously used for recovering condensables in vapor obtained in flash depressurization and vacuum evaporation/concentration stages of a urea recovery process.

SUMMARY OF THE INVENTION

According to the present invention, an efficient direct contact cooler replaces multiple expensive shell and tube coolers previously used in vacuum concentration of the urea product and condensation of the released vapors.

As a first embodiment, the present invention provides a method for recovering condensables in hot vapor from a urea vacuum evaporator. As step (a), the hot vapor from a urea vacuum evaporator is directly introduced below an absorption zone of an absorber unit. As step (b), a vapor stream is withdrawn overhead from the absorption zone to maintain subatmospheric pressure in the absorber unit. In step (c), an aqueous stream is introduced to the absorber unit above the absorption zone. As step (d), the vapor introduced in step (a) is contacted in the absorption zone with the aqueous stream introduced in step (c) to condense water, absorb ammonia and carbamate and wash urea from the vapor into the aqueous stream. In step (e) the aqueous stream from step (d) is collected. As step (f), water collected in step (e) is cooled and recirculated to the introduction step (c).

In one version of the present invention, the evaporator comprises first and second stage concentrators in series, and the vapor introduced in step (a) comprises respective first and second vapor streams therefrom. The first and second vapor streams are preferably introduced to a feed zone below the absorption zone. The absorption zone can comprise upper and lower stages, in which case the method preferably includes the steps of introducing the first vapor stream from the first stage concentrator to a lower feed zone below the lower absorption stage, and introducing the second vapor stream from the second stage concentrator to an upper feed zone between the upper and lower absorption stages, wherein the upper feed zone is in fluid communication between the upper and lower absorption stages for the upward and downward passage of respective vapor and liquid therethrough. The second vapor stream is preferably educted from the second stage concentrator into the upper feed zone using steam as motive fluid.

In a preferred embodiment, a vacuum seal is preferably maintained between the absorber unit and a tank for receiving the aqueous stream collected in step (e). The vacuum seal comprises a water-filled leg extending from below liquid level in the tank to an upper elevation below the absorption zone. The withdrawal step (b) preferably comprises ejecting vapor from the absorber unit with steam as motive fluid. A portion of the collected aqueous stream from step (e) is preferably withdrawn for urea hydrolysis and other process uses.

As another embodiment, the present invention provides a urea concentrating unit. As a first element, first and second stage urea vacuum evaporators are provided in series. As a second element, an absorption column including an absorption zone is provided. Means are provided for introducing vapor streams from the vacuum evaporators directly to the absorption column below the absorption zone. An overhead line is provided from the absorption column for withdrawing vapor from above the absorption zone to maintain a subatmospheric pressure in the absorption column. A tank is provided for receiving aqueous liquid from the absorption column comprising ammonia, carbamate and urea. A pump and line are provided for recirculating water from the tank to the absorption column above the absorption zone. A heat exchanger on the recirculation line is provided for cooling the recirculated water.

In a preferred embodiment, a feed zone is provided below the absorption zone in fluid communication with each of the vapor lines from the first and second stage vacuum evaporation. The absorption zone preferably has upper and lower absorption stages, a lower feed zone below the lower absorption stage in fluid communication with the vapor line from the first stage vacuum evaporator, and an upper feed zone between the upper and lower absorption stages in fluid communication with the vapor line from the second stage vacuum evaporator. The upper feed zone is in fluid communication between the upper and lower absorption stages for the respective upward and downward flow of vapor and liquid therethrough. The water recirculation line is in fluid communication with the upper absorption stage adjacent an upper end thereof. A steam eductor is preferably provided in the vapor line from the second vacuum evaporator to the upper feed zone for compressing vapor from the second vacuum evaporator to meet the pressure of the upper feed zone. A vacuum seal is preferably provided between the tank and the absorption zone including a liquid leg extending from below liquid level in the tank to an upper elevation below the absorption zone. A steam eductor is preferably provided in the overhead line from the absorption unit. The heat exchanger is preferably a plate-fin heat exchanger having a cold-side fluid comprising cooling water.

DETAILED DESCRIPTION OF THE INVENTION

Figure 1:
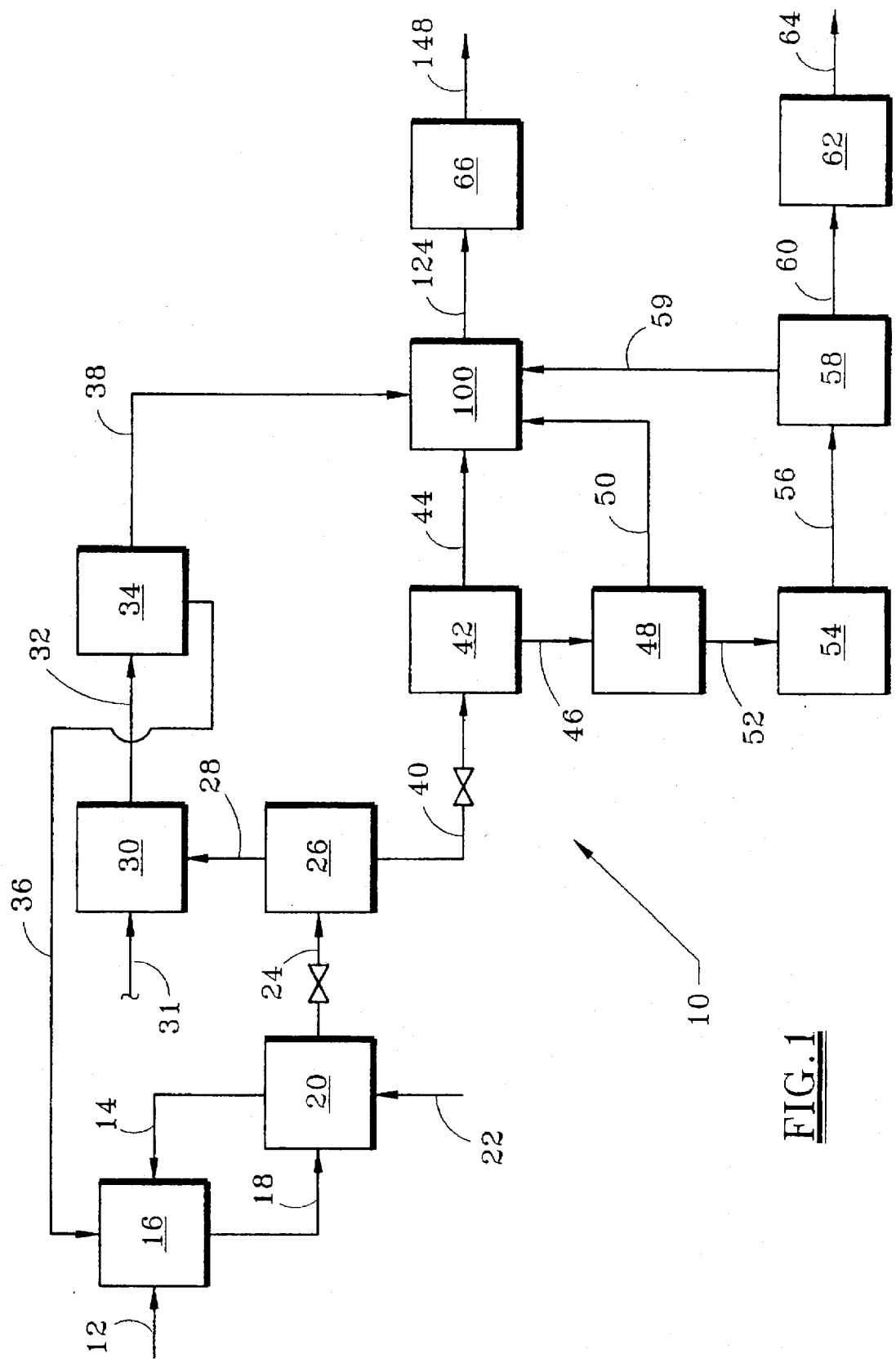
FIG. 1 illustrates a block process diagram of an embodiment of the urea recovery process of the present invention wherein the urea product is granulated.

Multiple large surface (e.g. shell and tube) condensers previously used to cool vapors released in a urea vacuum evaporation/concentration step of a urea process are replaced by a simple contact absorption tower to obtain significant capital and utility savings.

Referring to FIGS. 1–4, wherein like numerals reference like parts, urea is made in a process 10, 10' of the present invention by reacting ammonia and carbon dioxide at an elevated temperature (180°–195° C.) and pressure (14–20 MPa). A liquid ammonia stream introduced via line 12 and a carbon dioxide stream introduced via line 14 are combined directly in a reaction stage 16 to form ammonium carbamate, followed in a continuous fashion by dehydration of the carbamate to urea and water. The ratio of ammonia to carbon dioxide will vary from about 2.8 to 3.6:1 depending on the process being used, e.g. Stamicarbon or Snamprogetti. Per pass conversion typically ranges from 50–70 percent by weight of the carbon dioxide which is the limiting reactant.

An aqueous urea product stream produced by carbamate dehydration in the reaction stage 16 is directed via line 18 to a high pressure stripping stage 20 wherein the product stream is stripped at high pressure using an incoming reactant stream such as $CO_2$ introduced via line 22 to separate a first portion of the residual $CO_2$ and $NH_3$ therefrom. Effluent of the high pressure stripping stage 20 is then let down via line 24 to a low pressure stripping stage 26 to separate the bulk of the remaining residual $CO_2$ and $NH_3$ and produce a raw aqueous urea solution concentrated to about 70–80 percent by weight urea. The low pressure stripping stage 6 typically employs a stripping vapor generated by boiling a portion of the accumulated raw urea product.

Vapor from the low pressure stripping stage 26, consisting mostly of $NH_3$, $CO_2$ and $H_2O$, is removed via line 28 and cooled in a carbamate condensing stage 30 to form an aqueous solution of carbamate. If desired, condensate can be supplied to the condensing stage 30 via line 31. A two-phase stream containing carbamate condensate is passed via line 32 to a separation drum 34 and the carbamate condensate is returned to the urea reaction stage via line 36. Depending on process design criteria, a vapor stream comprising primarily ammonia, water, $CO_2$ and inert noncondensables is removed via line 38 from the carbamate condenser drum 34 for water condensation and ammonia removal in accordance with the granulation embodiment of FIGS. 1–2 or via line 38' for condensation and cleanup in an atmospheric absorber (not shown) in accordance with the prilling embodiment of FIGS. 3–4.

The raw aqueous urea solution produced by the low pressure stripping stage 26 is flashed adiabatically via line 40 to a flash drum 42 maintained at an atmospheric or subatmospheric pressure. The flashed urea solution typically comprises about 74.2 percent by weight urea, 0.5 percent by weight $CO_2$, 0.7 percent by weight $NH_3$ and 24.6 percent by weight water. As is well known, the pressure of the flash drum 42 and the path of subsequent urea concentrating steps can vary depending on the desired concentration of the final urea product.

Where a urea product having a concentration of about 96 percent by weight is desired for granulation, for example, the pressure of the drum 42 will typically be maintained at about 100 to 120 kPa(a). As seen in FIG. 1, vapor driven off the flashed urea solution comprises primarily ammonia, water, and $CO_2$ and is passed via line 44 for condensation and cleanup as mentioned for the vapor stream 38 above. Urea solution is withdrawn via line 46 to a pre-concentrating stage 48. Vapor produced from the stage 48 is removed via line 50 for water condensation and cleanup as mentioned for the vapor streams 38, 44 above. Urea solution effluent is withdrawn from the pre-concentrating stage 48 via line 52 to a storage tank 54, and then withdrawn via line 56 to a primary concentrating stage 58 operating under partial vacuum to evaporate water from the product solution. Vapor comprising ammonia, water, $CO_2$ and urea carry over (e.g. entrained and/or dissolved) is taken overhead via line 59 for condensation and cleanup similar to vapor streams 38, 44, 50. A urea product thus concentrated is removed via line 60 from the concentrating stage 58 to a finishing stage 62 for granulation into a form suited for handling and shipping. Urea product is removed via line 64.

In the practice of the present invention, the vapor streams 38, 44, 50, 59 evolved from the urea solution in the various purification and concentration stages 26, 42, 48, 58 mentioned above can be cooled by direct contact in a central absorption stage 100 operated under partial vacuum rather than by surface contact to condense the water and concurrently absorb ammonia, $CO_2$, inerts and urea carry over therefrom.

Figure 2:
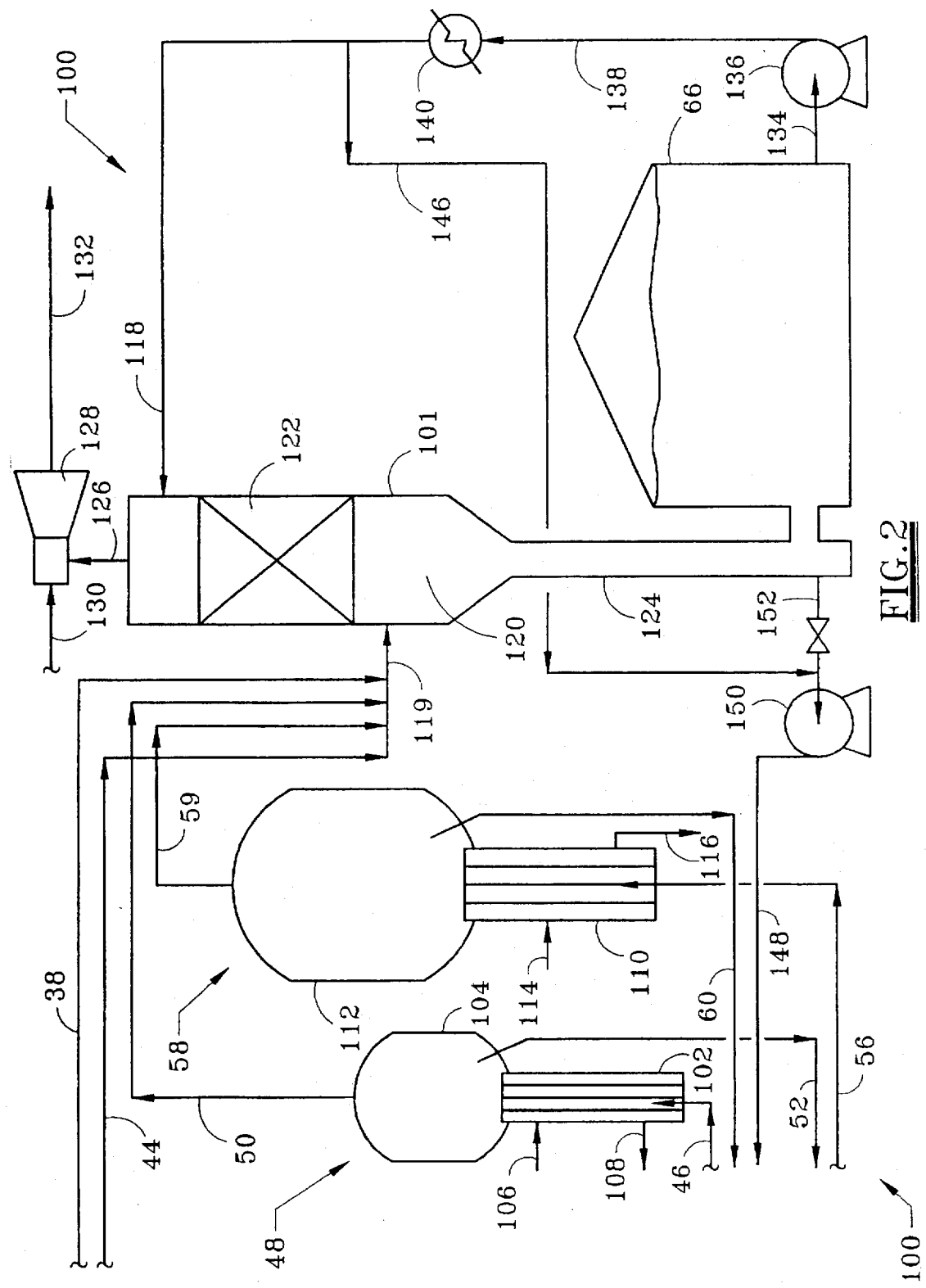
FIG. 2 illustrates a schematic detail of the process of FIG. 1 showing a central absorption tower of the present invention having a single stage.

As seen in FIG. 2, the urea stream 46 is adiabatically flashed in the pre-evaporation stage 48 to about 37 kPa(a) and 85° C., and then heated to about 90° C. by a pre-evaporator heater 102 to concentrate the solution in a separator 104. The partial vacuum in the pre-evaporation stage 48 is maintained by continuous condensation of the evolved vapor removed through line 50 to an absorption tower 101.

The heater 102 preferably takes the form of a shell and tube exchanger formed integrally to the pre-evaporator separator 104. Heat of evaporation of the pre-evaporation stage 48 is preferably supplied by heat generated in the urea formation stage 16 via tempered water introduced to the heater 104 on a shell side through line 106 and returned through line 108.

Following preconcentration, urea solution in the separator 104 concentrated to about 90 percent by weight urea is pumped to the primary evaporation stage 58 via the storage tank 54 as mention above. In the primary evaporation stage 58, the urea stream 56 is heated to about 133° C. by a primary evaporator heater 110 to concentrate the solution in a separator 112. The subatmospheric pressure in the evaporation stage 58 is maintained by continuous condensation of the evolved vapor removed through line 59 to the absorption tower 101.

The heater 110 preferably takes the form of a shell and tube exchanger formed integrally to the primary evaporator separator 112. Heat of evaporation of the primary evaporation stage 54 is preferably supplied by low pressure condensing steam introduced on a shell-side of the heater 110 through line 114. Steam condensate is removed via line 116. The concentrated urea product is removed from the separator 112 via line 60 for granulation.

In accordance with one embodiment of the present invention, the vapor streams 38, 44, 50, 59 produced by the urea concentrating steps 26, 48, 58 of the granulation process 10 are treated in the absorption tower 101 at a pressure of about 27.8 kPa(a) using a cool aqueous absorbent liquid introduced via line 118. The vapor streams 38, 44, 50, 59 are introduced via a feed line 119 to the absorption tower 101 at a feed zone 120 below an absorption zone 122 comprising suitable vapor-liquid contacting elements. In the absorption zone 122, most of the water, ammonia and $CO_2$ vapors, and any urea solids carry over from the feed stream 119 are absorbed and cooled by the absorbent stream 118.

The absorbent liquid stream 118 is circulated from the absorbent zone 122 to a holding tank 66 via a leg 124 submerged under the level of aqueous absorbent in the tank 66 to maintain a vacuum seal between the absorption tower 101 and the tank 66. Subatmospheric pressure in the tower 101 is maintained by drawing off noncondensed gases overhead via line 126. The vapor stream 126 leaves the absorber 101 at a pressure of about 24.5 kPa(a), is boosted to atmospheric pressure by an ejector 128, employing low pressure steam introduced via line 130 as the motive fluid, and passed via line 132 to an atmospheric absorber (not shown) to treat any remaining ammonia therein.

Absorbent liquid comprising primarily ammonia-containing water is withdrawn from the tank 66 via line 134, circulated by a pump 136 via line 138, through cooler 140 for dissipation of the heat of condensation against cooling water, fed to the tower 101 via line 118 and sent to other uses via line 146. The cooler 140 preferably comprises a plate-frame exchanger and cools the absorbent liquid to a temperature of about 35° C. A minor portion of the absorbent liquid can be circulated through line 148 by a pump 150 for other uses in the process 10, such as, for example, the carbamate condensation stage 30 via line 31.

Figure 3:
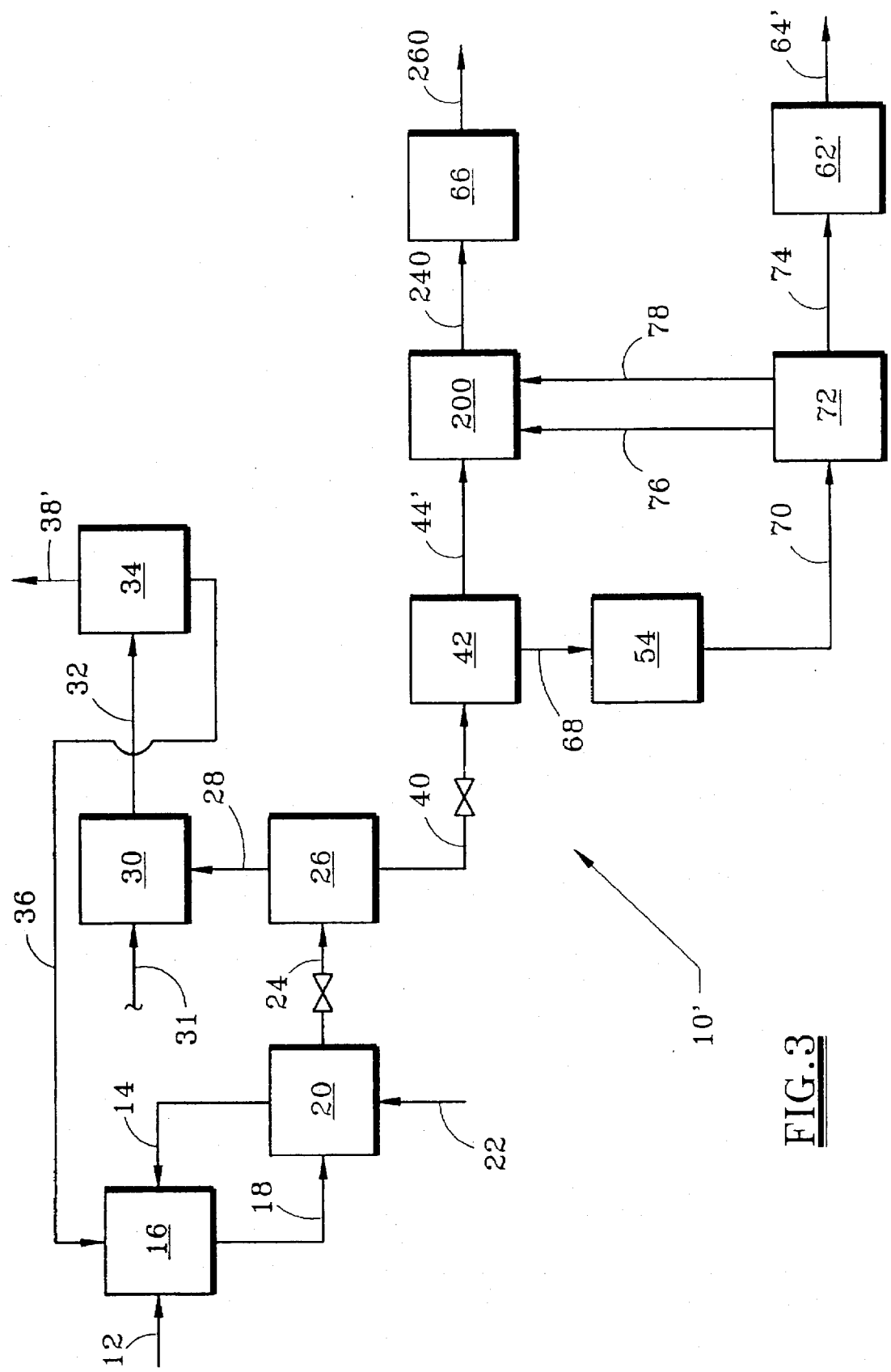
FIG. 3 illustrates a block process diagram of another embodiment of the present invention wherein the urea product is prilled.

For a urea product having a concentration up to about 99.7 percent by weight for prilling, for example, the drum 42 is preferably maintained at a subatmospheric pressure from about 45 to 55 kPa(a) and a vapor stream 44' is produced, as seen in FIG. 3. Urea solution is passed directly via line 68 to the storage tank 54, and then fed via line 70 to a generally dual stage urea concentrating unit 72 operating under partial vacuum to evaporate water from the product solution as mentioned above. A high concentration urea product is removed via line 74 from the concentrating stage 72 to the finishing stage 62' for prilling. Urea product is removed via line 64'. Vapor comprising ammonia, water and entrained urea are taken overhead via line(s) 76, 78 for condensation and cleanup.

Figure 4:
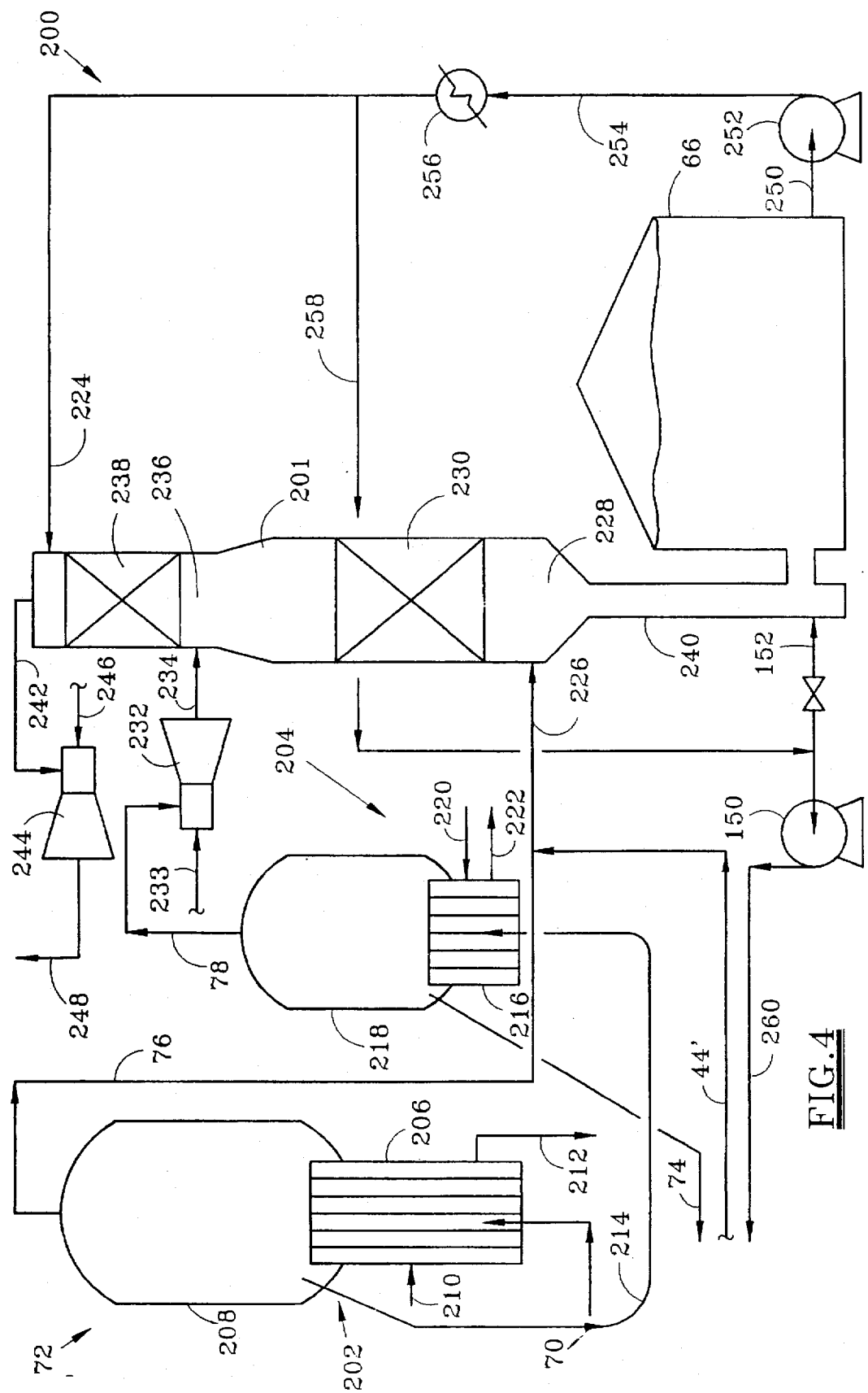
FIG. 4 illustrates a schematic detail of the process of FIG. 3 showing a central absorption tower of the present invention having dual stages.

As best seen in as seen in FIG. 4, the urea solution stream from the drum 42 is directed to the urea concentrating stage 72 having dual subatmospheric evaporation units 202, 204 operating in series to evaporate water from the product solution.

The urea solution stream 70 is pumped from the storage tank 54 to the first stage urea concentrating unit 202 operating at a subatmospheric pressure of about 37 kPa(a) and then heated to about 120° C. by a first stage heater 206 to concentrate the solution in a separator 208 to about 95 percent by weight urea. Subatmospheric pressure in the first evaporation stage 202 is maintained by continuous condensation of the evolved vapor removed through line 76 to an absorption tower 201.

The heater 206 preferably takes the form of a shell and tube exchanger formed integrally to the first evaporator separator 208. Heat of evaporation of the first evaporation stage 202 is preferably supplied by condensing steam introduced to the heater 206 on a shell side through line 210 and steam condensate removed through line 212.

Following the first concentration stage 202, urea solution in the separator 208 is flashed adiabatically via line 214 to the second stage unit 204 operating at a subatmospheric pressure of about 3.33 kPa(a). In the second concentrating stage 204, the urea solution from the first stage 202 is heated to about 134° C. by a second stage heater 216 to concentrate the solution in a separator 218 to about 99.7 percent by weight urea. The subatmospheric pressure in the second evaporation stage 204 is maintained by continuous condensation of the evolved vapor removed through line 78 to the absorption tower 201.

Similar to other evaporation stage heaters, the heater 216 preferably takes the form of a shell and tube exchanger formed integrally to the primary evaporator separator 218. Heat of evaporation of the secondary evaporation stage 204 is preferably supplied by low pressure condensing steam introduced to the heater 216 on the shell side through line 220. Steam condensate is removed via line 222. The purified urea product is removed from the separator 218 via line 74 for prilling in the handling stage 62' (see FIG. 3).

The vapor streams 44', 76, 78 produced by the urea concentrating steps 26, 72 of the prilling route are treated in the absorption tower 201 at pressure of about 10.0 kPa(a) using a cool aqueous absorbent liquid introduced via line 224. The relatively higher pressure vapor streams 44', 76 are preferably combined and introduced via line 226 to the absorption tower 201 at a lower feed zone 228 below a lower absorption stage 230. The vapor stream 78 has a lower pressure than the absorber 201 and is preferably boosted by an ejector 232 employing low pressure steam introduced via line 233 as the motive fluid. The boosted vapor stream from the low pressure separator 218 is preferably introduced via line 234 to an upper feed zone 236 below an upper absorption stage 238.

The lower and upper absorption stages 230, 238 typically comprise suitable vapor-liquid contacting elements. In the absorption stages 230, 238, the absorbent stream 224 cools and absorbs most of the water, ammonia and $CO_2$ vapors, and entrained urea solids from the feed streams 226, 234. The absorbent liquid stream 224 is circulated from the absorbent stages 230, 238 to the holding tank 66 via a leg 240 submerged under the level of aqueous absorbent in the tank 66 to maintain a vacuum seal between the absorption tower 201 and the tank 66.

Subatmospheric pressure in the tower 201 is maintained by drawing noncondensed gases overhead via line 242. The unabsorbed stream 242 from the top of the absorption tower 201 is boosted to about atmospheric pressure by an ejector 244 employing low pressure stream introduced via line 246 as the motive fluid, and passed to the atmospheric absorber (not shown) via line 248 to treat any remaining ammonia therein.

Absorbent liquid comprising primarily ammonia containing water is withdrawn from the tank 66 via line 250, circulated by a pump 252 via line 254 through cooler 256 for dissipation of the heat of condensation against cooling water, and fed to the tower 201 via line 224 and recirculated to the tank 66 via lines 258, 152. The cooler 256 preferably comprises a plate-frame exchanger and cools the cooled absorbent liquid to a temperature of about 30° C. A minor portion of the absorbent liquid can be circulated through line 260 by the pump 150 for other uses in the process 10'.

EXAMPLE

The impact of replacing vacuum surface coolers and ancillary equipment used for urea recovery with a contact cooler of the present invention is analyzed by computer simulation. A 1500 metric ton per day (MTPD) urea prilling route plant and a 2000 MTPD urea granulation route plant are used as a basis for the calculations. A material balance for the absorber towers 101, 201 of the present invention is presented in Table 1. Standard cost estimating programs are employed to calculate potential cost savings in utilities and capital equipment.

Adoption of the present invention poses no adverse impact in the operation of the urea or associated ammonia production units. There is a concomitant reduction of total investment cost for vessel manufacture and associated stainless steel piping, fittings, valves support structure, and the like process equipment since multiple units can be replaced by a single unit. In addition, replacement of surface condensers reduces the chance for fouling of the condenser tubes and manufacture of poor quality prilled product.

Improved cooling efficiency of the present contact and plate-fin coolers reduces the required cooling water recirculation rate. As a result, utility consumption of the urea recovery unit can be reduced. In addition, reduced recirculation rates permits the plant cooling water system including the inlet and return headers, above and underground piping, circulation pumps, and the like to have smaller size. Also a reduction in a cooling tower make-up water is obtained due to reduced circulation and blowdown from the cooling tower (not shown).

Further, process condensate (from the tank 76) can be used to supply lower temperature absorbent to the low pressure (4 bar) and atmospheric absorbers (not shown) to increase ammonia absorption and reduce plant emissions. Also, surface area of other process wide coolers (not shown) employing utility cooling water can be reduced due to the availability of utility cooling water at a lower temperature.

In the prilling route plant, several ejectors otherwise required to boost the pressure of the vapor streams to the surface condensers can be eliminated for a savings of low pressure steam. The addition of the contact cooler recirculation pump 136 increases an overall electrical power requirement which is more than compensated by other savings.

Utilities savings in the present process for both prilling and granulation routes are shown in Table 2.

TABLE 1

| | Granulation Route | | | | | | | |
|---|---|---|---|---|---|---|---|---|
| Process Stream | 59 | 134 | 126 | 118 | 50 | 146 | 44 | 38 |
| Urea (wt %) | 1–1.5 | 0.8–1.5 | 0.0 | 0.8–1.5 | 0.6–1 | 0.8–1.5 | — | — |
| Ammonia (wt %) | 1–2 | 4–8 | 12–15 | 4–8 | 6–10 | 4–8 | 27–32 | 35–40 |
| $CO_2$ (wt %) | 1–2 | 3–6 | 4–8 | 3–6 | 1.5–3 | 3–6 | 18–23 | 50–55 |
| $H_2O$ (wt %) | 92–97 | 85–90 | 13–18 | 85–90 | 85–90 | 85–90 | 48–53 | 6–10 |
| $N_2 + O_2$ (wt %) | 0.10–0.11 | — | 60–65 | – | 0.2–0.3 | — | — | 2.3–2.5 |
| TOTAL FLOW (kg/hr) | 25,085 | 1,436,078 | 121 | 1,394,585 | 9,032 | 41,060 | 5,498 | 1,466 |
| Temp. (°C.) | 133.0 | 53.0 | 35.0 | 35.0 | 90.0 | 35.0 | 103.2 | 82.3 |
| Pressure (kPa(a)) | 26.8 | 28.0 | 25.0 | 33.0 | 38.6 | 250 | 113.3 | 330 |

| | Prilling Route | | | | | |
|---|---|---|---|---|---|---|
| Process Stream | 226 | 234 | 242 | 250 | 224 | 258 |
| Urea (wt %) | 0.5–1 | 3–5 | 0.0 | 1–2 | 1–2 | 1–2 |
| Ammonia (wt %) | 5–8 | 2–4 | 20–25 | 4–8 | 4–8 | 4–8 |
| $CO_2$ (wt %) | 3–6 | 2–4 | 6–10 | 3–6 | 3–6 | 3–6 |
| $H_2O$ (wt %) | 85–92 | 88–93 | 30–35 | 83–88 | 83–88 | 83–88 |
| $N_2 + O_2$ (wt %) | 0.15–0.16 | 0.2–0.25 | 32–37 | — | — | — |
| TOTAL FLOW (Kg/hr) | 25,470 | 10,315 | 176 | 1,010,216 | 974,606 | 35,609 |
| Temp. (°C.) | 120.2 | 133.6 | 30.0 | 53.0 | 30.0 | 30 |
| Press. (kPa(a)) | 33.4 | 10.2 | 10.0 | 33.0 | 15.0 | 250 |

TABLE 2

| Source | Amount Saved |
| --- | --- |
| Prilling Case | |
| Steam for ejectors | 1.116 MMBTU/hr |
| Power for circulation pump 252 | −50.6 kW |
| Cooling water | 1069 m³ |
| Granulation Case | |
| Power for circulation pump 136 | −78.2 kW |
| Cooling water | 1028.8 m³ |

The capital cost saving is 3 to 5% of the urea plant inside battery limits, depending on prilling or the granulation route.

The present urea recovery process is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

We claim:

1. A method for recovering condensables in hot vapor from a urea vacuum evaporator, comprising the steps of:
   (a) directly introducing the hot vapor from the urea vacuum evaporator below an absorption zone of an absorber unit;
   (b) withdrawing a vapor stream overhead from the absorption zone to maintain subatmospheric pressure in the absorber unit;
   (c) introducing an aqueous stream to the absorber unit above the absorption zone;
   (d) contacting the vapor introduced in step (a) in the absorption zone with the aqueous stream introduced in step (c) to condense water, absorb ammonia and $CO_2$ and wash urea from the vapor introduced in step (a) into the aqueous stream introduced in step (c);
   (e) collecting the aqueous stream from step (d);
   (f) cooling and recirculating aqueous solution collected in step (e) to the introduction step (c); and
   (g) maintaining a vacuum seal between the absorber unit and a tank for receiving the aqueous solution collected in step (e), wherein the vacuum seal comprises a water-filled leg extending from below liquid level in the tank to an upper elevation below the absorption zone.

2. The method of claim 1, wherein the evaporator comprises first and second stage concentrators in series, and the vapor introduced in step (a) comprises respective first and second vapor streams therefrom.

3. The method of claim 2, wherein the first and second vapor streams are introduced to a feed zone below the absorption zone.

4. The method of claim 2, wherein the absorption zone comprises upper and lower stages, comprising:
   introducing the first vapor stream from the first stage concentrator to a lower feed zone below the lower absorption stage;
   introducing the second vapor stream from the second stage concentrator to an upper feed zone between the upper and lower absorption stages, wherein the upper feed zone is in fluid communication between the upper and lower absorption stages for the upward and downward passage of respective vapor and liquid therethrough.

5. The method of claim 4, comprising educting the second vapor stream from the second stage concentrator into the upper feed zone using steam as the motive fluid.

6. The method of claim 1, wherein the withdrawal step (b) comprises ejecting vapor from the absorber unit with steam as motive fluid.

7. The method of claim 1, comprising withdrawing a portion of the collected aqueous stream from step (e) for urea hydrolysis.

8. The method of claim 1 wherein the hot vapor in step (a) has a temperature above 90° C.

9. A urea concentrating unit, comprising:
   first and second stage urea vacuum evaporators in series;
   an absorption column including an absorption zone;
   means for introducing vapor streams from the vacuum evaporators directly to the absorption column below the absorption zone;
   an overhead means from the absorption column for withdrawing vapor from above the absorption zone to maintain a subatmospheric pressure in the absorption column;
   a tank for receiving aqueous liquid from the absorption column comprising ammonia, carbamate and urea;
   a pump and means for recirculating aqueous liquid from the tank to the absorption column above the absorption zone wherein the recirculated liquid contacts, cools, and condenses the vapor from the evaporators to form the aqueous liquid comprising ammonia, carbamate and urea;
   a heat exchanger on the recirculation means for cooling the recirculated aqueous liquid.

10. The urea concentrating unit of claim 9, comprising a feed zone below the absorption zone in fluid communication with each of the vapor introduction means from the first and second stage vacuum evaporation.

11. The urea concentrating unit of claim 9 wherein the absorption zone comprises upper and lower absorption stages, a lower feed zone below the lower absorption stage in fluid communication with the vapor stream introduction means from the first stage vacuum evaporator, and an upper feed zone between the upper and lower absorption stages in fluid communication with the vapor introduction means from the second stage vacuum evaporator, wherein the upper feed zone is in fluid communication between the upper and lower absorption stages for the respective upward and downward flow of vapor and liquid therethrough, and wherein the aqueous liquid recirculation means is in fluid communication with the upper absorption stage adjacent an upper end thereof.

12. The urea concentrating unit of claim 11, comprising a steam eductor in the vapor stream introduction means from the second vacuum evaporator to the upper feed zone for compressing vapor from the second vacuum evaporator to meet the pressure of the upper feed zone.

13. The urea concentrating unit of claim 9, comprising a vacuum seal between the tank and the absorption zone including a liquid leg extending from below liquid level in the tank to an upper elevation below the absorption zone.

14. The urea concentrating unit of claim 9, comprising a steam eductor in the overhead means from the absorption unit.

15. The urea concentrating unit of claim 9, wherein the heat exchanger is a plate and frame heat exchanger having a cold-side fluid comprising cooling water.

16. A method for recovering condensables in hot vapor from a urea vacuum evaporator comprising first and second stage concentrators in series, comprising the steps of:

(a) introducing first and second vapor streams from the respective first and second stage concentrators below an absorption zone of an absorber unit comprising upper and lower absorption zones wherein the first vapor stream is introduced to a lower feed zone below the lower absorption zone, the second vapor stream is introduced to an upper feed zone between the upper and lower absorption zones, and the upper feed zone is in fluid communication between the upper and lower absorption zones for the upward and downward passage of respective vapor and liquid therethrough wherein the second vapor stream from the second stage concentrator is educted into the upper feed zone using steam as the motive fluid;

(b) withdrawing a vapor stream overhead from the upper absorption zone to maintain subatmospheric pressure in the absorber unit;

(c) introducing an aqueous stream to the absorber unit above the upper absorption zone;

(d) contacting the vapor introduced in step (a) in the upper and lower absorption zones with the aqueous stream introduced in step (c) to condense water, absorb ammonia and $CO_2$ and wash urea from the vapor introduced in step (a) into the aqueous stream introduced in step (c);

(e) collecting the aqueous stream from step (d);

(f) cooling and recirculating at least a portion of the aqueous stream collected in step (e) to the introduction step (c).

17. The method of claim 16, including maintaining a vacuum seal between the absorber unit and a tank for receiving the aqueous stream collected in step (e), comprising a water-filled leg extending from below liquid level in the tank to an upper elevation below the lower absorption zone.

18. The method of claim 16, wherein the withdrawal step (b) comprises ejecting vapor from the absorber unit with steam as motive fluid.

19. The method of claim 16, comprising withdrawing a portion of the collected aqueous stream from step (e) for urea hydrolysis.

20. The method of claim 16 wherein the hot vapor in step (a) has a temperature above 90° C.

* * * * *